United States Patent [19]

Reynolds et al.

[11] 4,047,526
[45] Sept. 13, 1977

[54] AUTOLOGOUS BLOOD SYSTEM AND METHOD

[75] Inventors: Gordon S. Reynolds, Bountiful; Karl A. Pannier, Jr.; James L. Sorenson, both of Salt Lake City, all of Utah

[73] Assignee: Sorenson Research Co., Inc., Salt Lake City, Utah

[21] Appl. No.: 580,087

[22] Filed: May 22, 1975

[51] Int. Cl.² .............................................. A61M 5/00
[52] U.S. Cl. .................................. 128/214 R; 128/276
[58] Field of Search ........... 128/214 R, 214 A, 214 B, 128/214 C, 214 D, 214.2, 276, DIG. 3, 231, 232, 278

[56] References Cited

U.S. PATENT DOCUMENTS

| | | | |
|---|---|---|---|
| 3,021,841 | 2/1962 | Burke | 128/214 C |
| 3,398,743 | 8/1968 | Shalit | 128/231 |
| 3,492,991 | 2/1970 | Dyer | 128/214 R |
| 3,896,733 | 7/1975 | Rosenberg | 128/214 R |

*Primary Examiner*—Richard C. Pinkham
*Assistant Examiner*—William R. Browne
*Attorney, Agent, or Firm*—H. Ross Workman; J. Winslow Young

[57] ABSTRACT

An autologous blood system comprising at least two interconnected blood receptacles, the first of which is evacuated and connected to a suction device for aspirating blood. The second receptacle takes blood from the first by overcoming the vacuum in the first without interrupting the ability of the suction device to simultaneously aspirate blood. An infusion set is connected to the second receptacle to permit simultaneous collection of the blood from the patient and infusion of the blood back into the patient. The method includes aspirating blood from the patient and collecting blood in the first receptacle. Blood is thereafter transferred to the second receptacle by overcoming the vacuum in the first receptacle without interrupting the ability of the suction device to simultaneously aspirate blood. Blood is then returned to the patient either with or without disconnecting the second receptacle from the first, the infusion step taking place concurrently with blood collection.

28 Claims, 8 Drawing Figures

AUTOLOGOUS BLOOD SYSTEM AND METHOD

BACKGROUND

1. Field of the Invention

The invention relates to apparatus and methods for autologous blood transfusion.

2. The Prior Art

Homologous blood transfusion is the well-known technique of collecting blood from a donor and thereafter storing the blood for later infusion into another patient. For many years, homologous blood transfusion has been the standard technique for replacing a patient's blood after surgery, obstetrical complications, traumatic hemorrhage and the like.

Homologous blood transfusion has evidenced a number of serious complications. For example, frequently elective surgical procedures must be postponed because of the unavailability of compatible homologous blood. In smaller towns and cities, there is frequently a lack of qualified donors. Also in larger metropolitan areas, there is a great need for quantities of blood to cover trauma situations and the increasing number of elective major surgical procedures. It is well-known that homologous blood must be cross matched to ascertain compatibility before the homologous blood is administered to a patient. Cross matching is an expensive and time consuming procedure and is not always effective in detecting blood incompatibility.

At present, the most serious complication due to homologous blood transfusion is post-transfusion hepatitis. The National Heart and Lung Institute has reported hundreds of deaths and thousands of cases of incapacitating illness resulting from post-transfusion hepatitis. Other complications, well-known in homologous blood transfusion, include isoimmunization, transmission of disease, incompatibility, hemolytic reactions and over transfusion.

These problems are substantially circumvented through the technique of autologous blood transfusion. Autologous transfusion is defined as the reinfusion of the patient's own blood. The desirability of autologous transfusion has been acknowledged for many years. Structure accommodating autologous transfusion is disclosed in applicant's U.S. Pat. No. 3,866,608. Until this present invention, however, no structure and method has been known which would accommodate reinfusion of a patient's blood without interrupting the ability to simultaneously collect the blood. Further, until this present invention, no prior art is known which provides a sterile, closed extracorporeal blood circuit for collecting the patient's blood and reinfusing the blood back into the patient.

BRIEF SUMMARY AND OBJECTS OF THE INVENTION

The present invention comprises novel apparatus and method for collecting a patient's blood in a first receptacle, transferring the patient's blood to a second receptacle and thereafter reinfusing the patient without interrupting the collection process in the first receptacle.

It is, therefore, a primary object of the present invention to provide improvements in autologous blood transfusion.

It is another object of the present invention to provide a closed extracorporeal blood circuit defining a sterile blood path from collection to reinfusion.

One still further object of the present invention is to provide an autologous blood system and method accommodating continuous availability of suction at the blood aspiration site during collection and reinfusion of the blood.

One still further valuable object of the present invention is to provide structure and method accommodating reinfusion of blood simultaneous with collection of the blood.

Another important object of the invention is to provide a sterile environment including filter for microorganisms to isolate the collection container from the vacuum line.

A further object of the present invention is to provide structure and method for interchanging second receptacles to accommodate the filling of several separate units from the first receptacle without requiring interruption of the blood collection process.

It is a further object of the present invention to provide structure and method for transferring blood from a first container to a second container by overcoming the vacuum pressure in the first container without requiring interruption of the blood collection process.

These and other objects and features of the present invention will become more fully apparent from the following description and appended claims taken in conjunction with the accompanying drawing.

DETAILED DESCRIPTION OF THE PREFERRED EMBODIMENTS

THE APPARATUS

Figure 1:
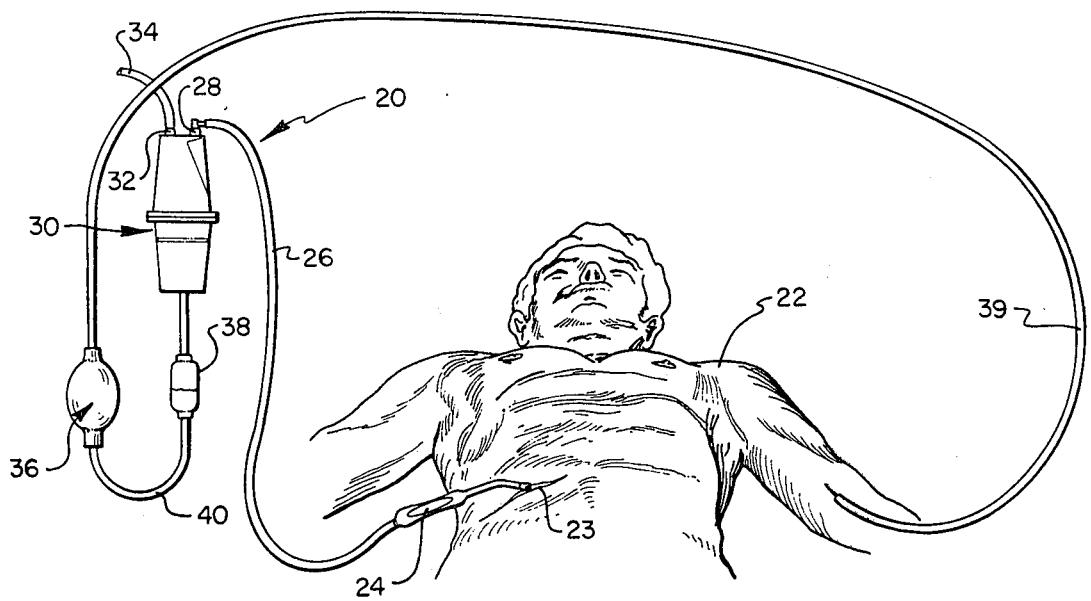
FIG. 1 is a schematic representation of one preferred embodiment of the invention illustrating structure and method for simultaneously collecting and infusing a patient's blood.

Attention is now directed to the drawing wherein like numerals represent like parts throughout. Referring generally to FIG. 1, the autologous blood transfusion system generally designated 20 is schematically illustrated. The purpose for the autologous system 20 is to recover and reinfuse the blood of a patient 22. Normally, the source of blood from the patient will be through a wound or surgical incision represented at 23. Commonly, autologous blood transfusion has its greatest value under circumstances where great amounts of blood would normally be lost in a short period of time from the patient. A number of vascular, thoracic and abdominal surgeries could come within this category. Another significant area deals with hemorrhagic trauma resulting from injury to the patient. In either event, blood can normally be collected near the hemorrhage site.

It is presently preferred that the blood be collected with an aspiration wand 24 as is conventional. The aspiration wand 24 is connected by an elongated tube 26 to the inlet port 28 of a first receptacle generally designated 30. The first receptacle 30 has a vacuum port 32 conventionally connected to a vacuum line 34 which communicates with a conventional vacuum source (not shown).

The first receptacle 30 is evacuated through the vacuum line 34 so as to create a suction in the aspiration wand 24 and tube 26. Thus, blood is aspirated at the wand 24 and deposited in the first receptacle 30. It is presently preferred that the aspiration wand 24 be provided with the capability of mixing anticoagulant with the aspirated blood as disclosed in our copending application Ser. No. 555,008 filed Mar. 3, 1975.

After the blood has been collected in the first receptacle, it must be communicated to a second receptacle generally designated 36. In the illustrated embodiment, a conventional blood filter 38 is interposed in the connecting conduit 40 between the first receptacle 30 and the second receptacle 36.

It is apparent by reference to FIG. 1 that without some force being exerted upon the blood, the blood will not move out of the first receptacle 30 into the second receptacle 36. Failure of the blood to naturally transfer into the second receptacle results because there is a significant negative pressure within the first receptacle, normally on the order of magnitude of 30 millimeters of mercury (mm Hg). Further, when the second receptacle is coupled directly into the patient's vein through the infusion set 38, the patient's blood pressure will discourage blood flow in the extracorporeal circuit in the clockwise direction as shown in FIG. 1. Structure must be provided, therefore, which will facilitate transfer of blood from the first receptacle 30 to the second receptacle 36.

Figure 2:
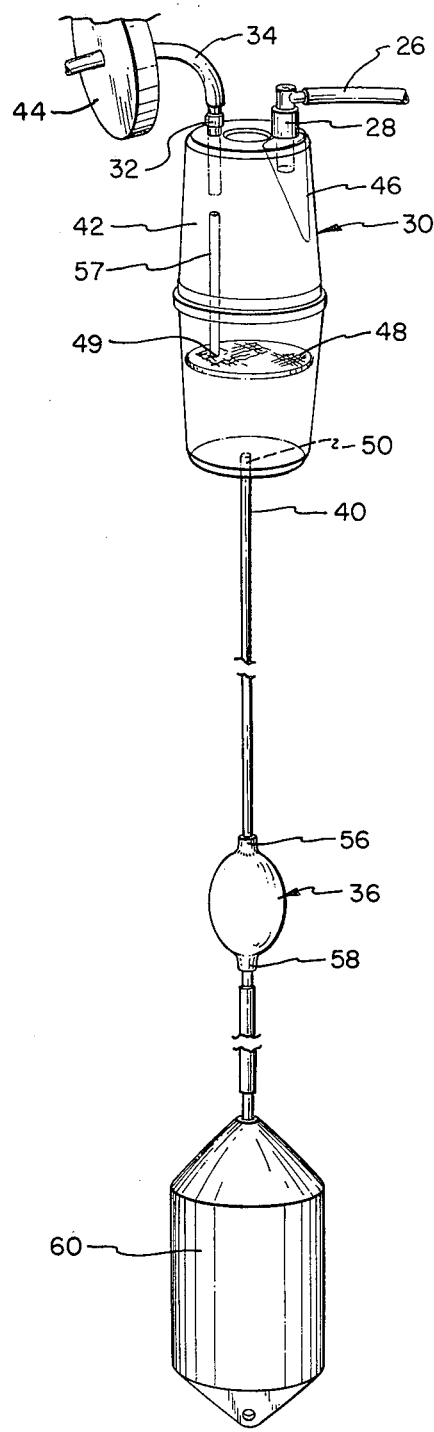
FIG. 2 is a fragmentary schematic perspective illustration of a presently preferred system embodiment of the invention.

Referring now particularly to FIG. 2, the first receptacle 30 is illustrated as a rigid, transparent plastic container. The top or cap 42 of the container is provided with diametrally opposed ports 28 and 32. The port 32 is connected through the vacuum line 34 to a vacuum source (not shown). It is presently preferred that the filter 44, capable of filtering microorganisms, be situated in the vacuum line 34 so as to preclude migration of contaminating microorganisms along the vacuum line 34 to the interior of the first receptacle 30.

The inlet port 28, as described above, is connected to the tube 26 (see FIG. 1). Blood passing through the tube 26 enters the interior of the first receptacle 30 at the port 28. Conventionally, a filter 46 initially filters blood emerging into the first receptacle 30.

It has been found desirable to interpose an additional filter 48 across the first receptacle 30. The additional filter 48 is preferably situated so as to minimize air turbulence in the blood accumulated in the receptacle 30. While the filter 48 is illustrated in the lower part of the receptacle, clearly it can be placed at any convenient location. The filter 48 is provided with a vent 49 there through which, in cooperation with a suitable standpipe 57 minimizes the formation of an air lock in the lower portion of receptacle 30.

While the first receptacle 30 has been described as a rigid container, it may also be desirable to use a flexible plastic container which has supporting structure (not shown) so as to resist collapse under the vacuum imposed in the vacuum line 34. In order for the first receptacle to function properly, it must resist significant deformation upon imposition of the normal blood collection vacuums, e.g. on the order of 30 mm Hg. The bottom of the receptacle 30 defines a downwardly projecting hollow boss 50 which serves as a coupling site for connecting conduit 40.

The second receptacle 36 is located downstream from the receptacle 30 and is coupled in air-tight relation with connecting conduit 40. The second receptacle 36 in the embodiment of FIGS. 1 and 2 includes a rubber bulb which is manually collapsible. Significantly, the rubber bulb is constructed of a resilient material, the resilience being chosen to exceed the vacuum or negative pressure normally developed in the first receptacle 30. Thus, when the second receptacle 36 is collapsed and thereafter released, the resilience of the receptacle 36 will overcome the negative pressure in the first receptacle 30 and draw blood located in the receptacle 30 through the connecting conduit 40 into the second receptacle 36.

It is presently preferred that a check valve 56 be mounted between the first and second receptacles, the check valve 56 being of conventional well-known construction. An example of a suitable check valve is found in U.S. Pat. No. 3,742,952. The check valve is constructed to limit the flow of blood unidirectionally from the first receptacle 39 to the second receptacle 36 and to prevent retrograde flow. A second check valve 58 of conventional construction is located downstream from the second receptacle 36. While automatic check valves have been described as preferred, suitable manual clamps such as illustrated schematically in FIGS. 3 and 4 could be used.

Desirably, the second receptacle 36 may be connected directly to an infusion set 39 as shown in FIG. 1. This would be the preferred procedure when it is desired to infuse blood into the patient simultaneously with collection of the blood. Alternatively, however, the second receptacle 36 may be connected to a blood storage container 60 as shown in FIG. 2. The container 60 may be a plastic blood collecting bag or other suitable container for maintaining and storing blood. In this FIG. 2 embodiment, the resilient bulb 36 serves the function of overcoming the negative pressure in receptacle 30 so as to transfer the blood into container 60. In the embodiment illustrated in FIG. 2, the resilient bulb 36 could be replaced with other suitable structure for overcoming the negative pressure in receptacle 30, e.g. a blood pump. The container 60 is filled by manually collapsing the second receptacle 36 so as to force blood unidirectionally from the first receptacle 30 into the container 60. Preferably the container 60 is removably attached to the output of the receptacle 36 so that the blood in container 60 can be reinfused into the patient. Notably, detachment of the container 60 from the second receptacle 36 will not adversely interrupt the collection of blood in the first receptacle 30.

Figure 3:
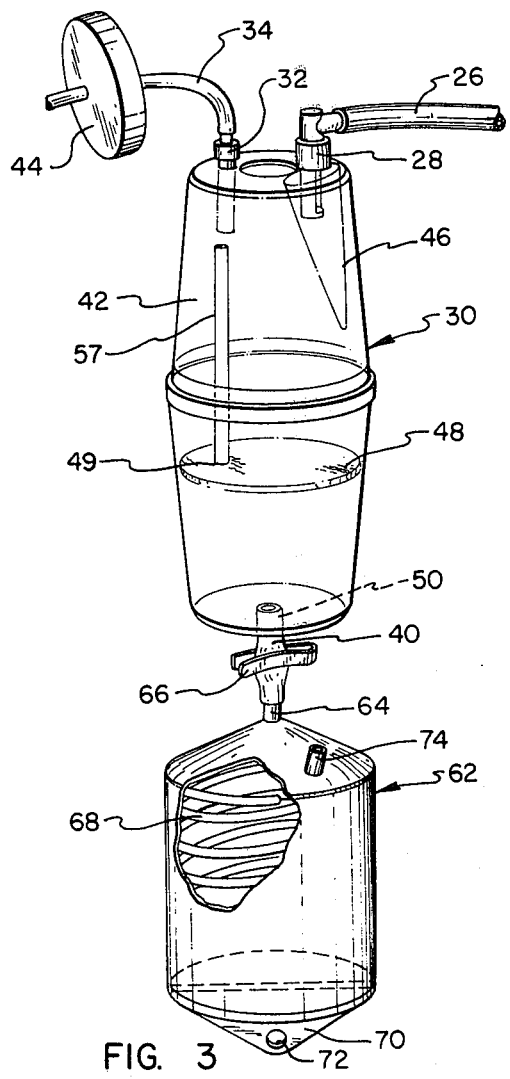
FIG. 3 is a fragmentary perspective view of first and second receptacles connected together, portions being broken away to reveal interior structure.

Another preferred embodiment of the present invention is illustrated in FIG. 3. In FIG. 3, the collapsible bulb 36 is substituted with a second receptacle embodiment generally designated 62. The second receptacle 62 is constructed of a flexible plastic material and presents a hollow coupling 64 communicating the interior of the receptacle 62 with the connecting conduit 40. Preferably the connecting conduit 40, in this embodiment, is formed of a rubber latex or like material which can be selectively sealed closed with a manual clamp 66. Interiorly, the second receptacle 62 is provided with a coiled forming member 68. The coiled forming member 68 is manually collapsible to render the receptacle 62 in a substantially condensed configuration similar to that illustrated in full lines in FIG. 7. The forming member 68 is manufactured of resilient material, the magnitude of the resilience being selected to overcome the negative pressures normally exerted upon the interior of the first receptacle 30.

The second receptacle 62 is provided with a suspension tab 70 having an aperture 72 therein which permits the receptacle 62 to be suspended upside down for reinfusion of blood after the receptacle 62 has been filled. To facilitate reinfusion, an access port 74 is provided and suitable venting structure (not shown) may be supplied, as is conventional. The access port 74 is normally sealed but can be penetrated with a conventional coupling of an infusion set for reinfusion of the blood into the patient 22.

In the operation of this embodiment, the first receptacle 30 is evacuated in the manner described above. Either before attachment of the second receptacle 62 or before aspiration of blood into the first receptacle, the receptacle 62 is collapsed against the bias of the coiled forming member 68. The clamp 66 is then placed upon the connecting conduit 44 thereby forming an air-tight seal and maintaining the second receptacle 62 in a collapsed configuration. As blood is aspirated into the first receptacle 30, clamp 66 may be removed permitting the forming member 68 to expand and draw the blood within the first receptacle 30 into the second receptacle 62.

When the second receptacle 62 is filled, it is a simple matter to reclamp the conduit 40, remove the second receptacle 62 and thereafter insert an additional similar second receptacle. The hollow coupling 64 may also be provided with a clamp 66 (see FIG. 4). Clearly, if desired, the manual clamp 66 may be substituted with a conventional check valve as described above which permits only unidirectional flow between the first and second receptacles.

Figure 4:
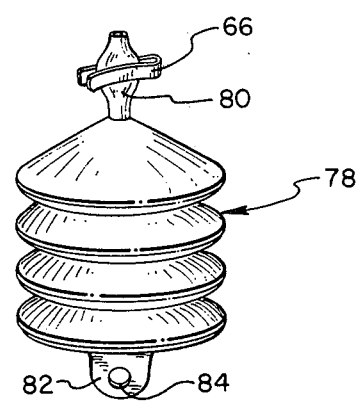
FIG. 4 illustrates an alternative second receptacle embodiment usable with the first receptacle structure of FIGS. 2 and 3.

FIG. 4 illustrates another suitable second receptacle embodiment generally designated 78. In this embodiment, the second receptacle is formed of resilient plastic material formed in the configuration of a bellows. A hollow coupling 80 may be used to attach the second receptacle 78 to the connecting tubing 40 which depends from the first receptacle 30. Desirably a tabe 82 having an aperture 84 depends from the receptacle 78 at the bottom thereof so as to provide a means of suspending the receptacle 78, when filled with blood, to facilitate infusion of the blood back into the patient. Conventional access and venting structure may also be provided in receptacle 78.

Figure 7:
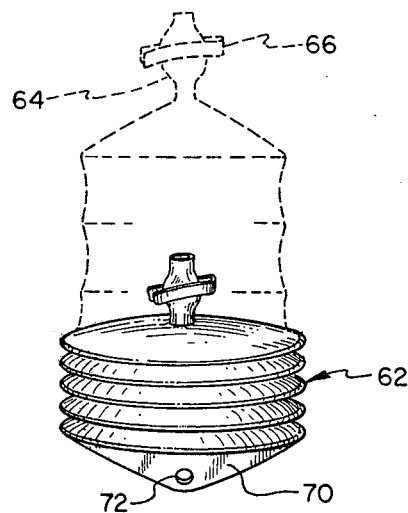
FIG. 7 is a perspective view of the second receptacle of FIG. 3 illustrated in the collapsed configuration.

In the operation of this embodiment, the second receptacle 78 is collapsed against the bias of the bellows construction in the same manner described in connection with the receptacle 62, above and as represented in FIG. 7. Notably, the resilience of the receptacle 78 must be chosen to overcome the negative pressure generated within the first receptacle 30. After the collapsed receptacle 78 has been attached to the first receptacle 30, blood will be urged therein in a manner similar to that described above in connection with receptacle 62.

Figure 5:
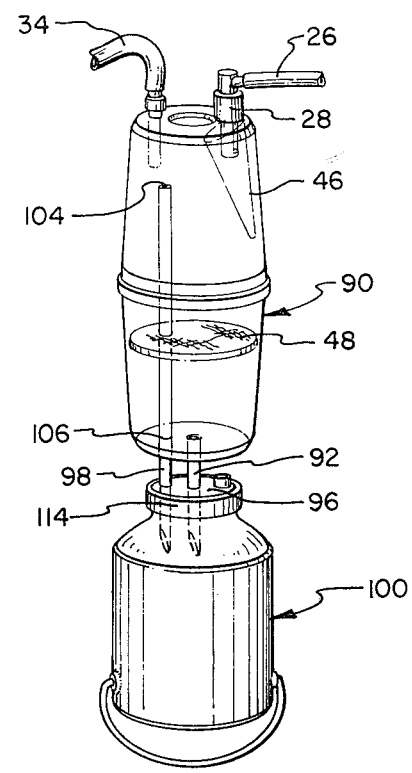
FIG. 5 is a fragmentary perspective illustration of still another preferred embodiment of the invention, the first and second receptacles being illustrated in the coupled relationship.
Figure 6:
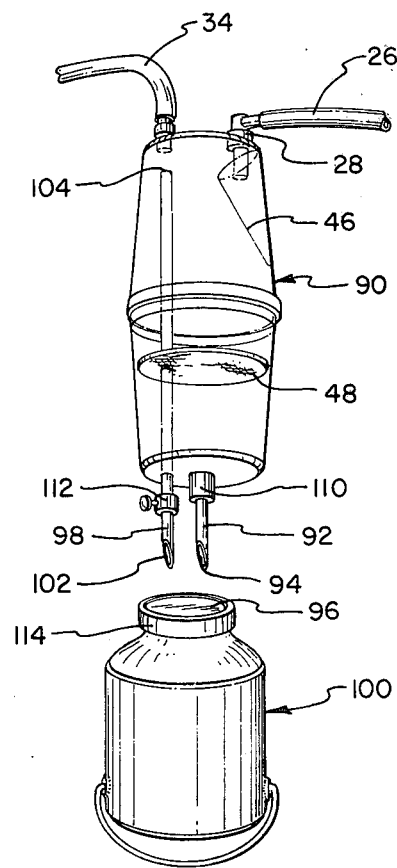
FIG. 6 is a perspective illustration of the embodiment of FIG. 5 in the uncoupled relationship, the first receptacle being rotated slightly to reveal the location of valving structure.

Attention is now directed to FIGS. 5 and 6. The embodiment of FIGS. 5 and 6 is similar to the embodiment of FIGS. 3 and 4 except as to the structure for overcoming the negative pressure in the first receptacle. In FIG. 5, the first receptacle generally designated 90 is structurally similar to the first receptacle generally designated 30 (FIG. 3) except that two substantially rigid spikes are attached thereto. Spike 92 is interiorly hollow and opens to the interior of the first receptacle 90. The spike is bevelled at 94 to facilitate penetration through a rubber cap 96 of second receptacle 100 as will be hereinafter more fully described.

Spike 98 is likewise hollow and is bevelled at 102. The spike 98 is elongated so as to project a substantial distance to the interior of the first receptacle 90, the length of the spike 98 being chosen so that the orifice 104 is situated well above the maximum normal blood level within the first receptacle 90. The junction of the receptacle 90 and the spike 98 is sealed at 106 to assure a fluid and air-tight coupling.

As shown best in FIG. 6, the spike 92 is provided with a check valve 110 permitting unidirectional fluid flow from the first receptacle 90 to the second receptacle 100. The spike 98 is provided with a two way valve 112 which is manually operable between open and closed positions.

The second receptacle 100 may be a conventional blood collection bottle or other rigid container. Container 100 has a rubber cap 96 held in place by a suitable metal ring 114, as is conventional. The rubber cap 96 is penetrable by the spikes 92 and 98 and the openings formed by the spikes can be used as an attachment site for the infusion set 39.

In the operation of this embodiment, the second receptacle 100 is cleansed particularly at the cap 96 to remove bacteria and contaminants. The valve 112 is maintained in the closed state and spikes 92 and 98 are caused to penetrate the cap 96. As blood accumulates in the first receptacle 90, the valve 112 is switched to the open state which has the effect of evacuating the second receptacle 100 whereupon the weight and turbulence in the blood carried by the firsr receptacle 90 will urge the blood through the spike 92 into the second container 100.

When the second container 100 is filled, the valve 112 may be switched closed permitting the receptacle 100 to be removed and another similar receptacle to be substituted therefor.

While the check valve 110 is illustrated as desirable, it is pointed out that under most conditions even if the check valve 110 is omitted, the receptacle 100 may be removed without loss of blood from the receptacle 90. The negative pressure maintained within the receptacle 90 will prevent the blood from flowing out of the spike 92. Thus, the receptacle 100 can be easily exchanged with a similar receptacle without adversely affecting the ability of the first receptacle 90 to continue to collect blood from the patient.

THE METHOD

Figure 8:
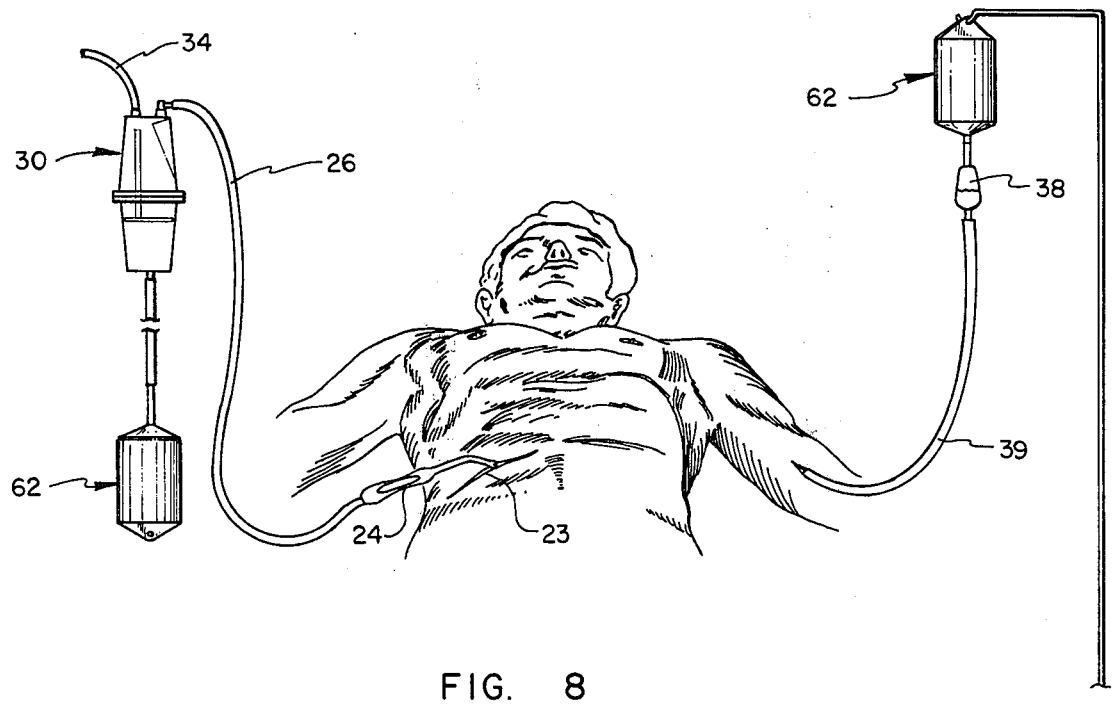
FIG. 8 is a schematic representation of another preferred embodiment of the invention illustrating structure and method for simultaneously collecting and infusing a patient's blood.

The method of the present invention may be practiced in two related ways as represented by FIGS. 1 and 8. In both embodiments, the blood aspirated from the patient 22 is conducted through a sterile, closed extracorporeal blood circuit. In FIG. 1, the blood is aspirated at the wand 24, conducted through the tube 26 and deposited in the first receptacle 30. Prior to actual infusion of the blood into the patient, air may be easily expelled from the blood delivery system by manually squeezing the second receptacle 36 to force air out of the receptacle 36, the infusion set 39 and the connecting tubing. Because the blood filter 38 and second receptacle 36 are spaced somewhat from the first receptacle 30, air is significantly more easily purged from the system. Thus, the maximum amount of blood can be returned to the patient without the risk of air embolism.

When the air has been purged from the system, the infusion set 39 is connected by venipuncture or the like into the cardiovascular system of the patient 22. As the receptacle 36 is forcefully collapsed, blood will be urged through the infusion set 39 into the patient. The resilience of the second receptacle 36 will then cause the receptacle to expand to its original position thereby drawing blood from the first receptacle 30 into the second receptacle 36.

Clearly, successive collapse and recovery of the second receptacle will deliver blood to the patient without interfering with the ability of the wand 24 and receptacle 30 to collect blood. The extracorporeal blood system is sterile and over transfusion is significantly reduced inasmuch as the only blood conducted back to the patient is that which was taken out. Hemodilution resulting from contributions of anticoagulant and the like is minimal.

The second embodiment, illustrated in FIG. 8, differs from the first primarily in that the second receptacle 60, 62, 78 or 100 is separated from the first prior to infusing the blood back into the patient 22. Also, the second receptacle may be used to force blood into a suitable delivery container as illustrated in FIG. 2. It is of significance that the second receptacles are provided with structure which urges the blood into the second receptacle without interrupting the suction at the wand 24. After the second receptacle has been filled from receptacle 30, it may be removed and another second receptacle attached to the first receptacle 30 without interrupting blood collection. The second receptacle may then be used to reinfuse the blood into the patient 22 simultaneously with blood collection at the wand 24, as shown in FIG. 8.

Sterile collection and reinfusion of autologous blood in accordance with the described methods is highly advantageous. Because the system is closed, extraneous contamination is minimized without undue effort. Placing a filter for microorganisms in the vacuum line 34 prevents contamination of the first receptacle 30 by the external vacuum source. Accordingly only the air aspirated with blood at the patient site 23 is permitted to mingle with collected blood. This aspirated air is derived from the sterile surgical field, or at least contains no more contamination than the patient is already exposed to at the site 23. Customary aseptic care in use of the infusion set 39 will maintain the blood circuit in a sterile condition. Thus, according to the present invention, autologous blood can be collected and infused without exposing the blood to the ambient.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. An autologous blood collection system comprising: means for aspirating blood from a patient; a first blood-receiving receptacle comprising means connected to the aspirating means for conducting blood from a patient to the interior of the first receptacle, means for imposing a continuous negative pressure within the first receptacle of sufficient magnitude to accommodate continuous aspiration of blood through the aspirating means, the first receptacle being sufficiently rigid that it will not significantly collapse upon imposition of the negative pressure; a second blood-receiving receptacle connected to the first by a hollow conduit which communicates the interior of the second receptacle with the interior of the first near the bottom of the first receptacle, the second receptacle comprising resilient means having sufficient resiliency for overcoming the continuous negative pressure in the first receptacle so as to forcibly transfer blood in the first receptacle to the second receptacle, said resilient means comprising means for infusing the blood in the second receptacle into the patient and additional means between said second receptacle and said first receptacle for permitting uninterrupted continuous negative pressure in the first receptacle during autologous blood collection.

2. An autologous blood collection system as defined in claim 1 wherein said second blood-receiving receptacle is normally exposed to the atmosphere as blood is collected in the first blood-receiving receptacle, the second receptacle being selectively separable from the first.

3. An autologous blood collection system as defined in claim 1 further comprising valve means between the first and second receptacles which valve means insure unidirectional blood flow from the first to the second receptacle so that blood can be delivered out of the second receptacle directly into the patient without first separating the receptacles from each other.

4. An autologous blood collection system as defined in claim 1 wherein said first blood-receiving receptacle comprises means for filtering the blood aspirated from the patient, said filtering means being transversely interposed between the inlet and outlet to the first receptacle so as to deflect at least a portion of the downwardly directed air entering the first blood-receiving receptacle from the aspirating means away from the blood filtered through the filtering means so as to minimize air agitation of the filtered blood in the first receptacle.

5. An autologous blood collection system as defined in claim 4 wherein said filtering means comprises venting means providing an air path through the filtering means to minimize air lock in the first blood-receiving receptacle.

6. An autologous blood collection system as defined in claim 1 wherein said aspirating means, first blood-receiving receptacle, second blood-receiving receptacle and infusing means comprise an extracorporeally closed blood circuit which is sterile.

7. An autologous blood collection system as defined in claim 6 further comprising a filter for microorganisms situated between the first blood-receiving receptacle and the means for imposing a negative pressure within the first receptacle so as to minimize migration of contaminating microorganisms to the interior of the first receptacle.

8. An autologous blood collection system comprising a closed extracorporeal blood circuit for collecting a patient's blood and delivering the collected blood to the same patient, the blood circuit comprising:
  means for aspirating blood from the patient;
  first means for collecting the aspirated blood, said first collecting means communicating with the aspirating means and means for continuously imposing a negative pressure in the first collecting means sufficiently to accommodate continuous aspiration of the blood;
  second means for collecting the aspirated blood, said second means comprising third means for transferring the blood in the first collecting means into the second collecting means by overcoming the continuous negative pressure in the first receptacle; and
  fourth means between said first means and said second means for facilitating infusion of blood into the patient from the second collecting means without interrupting the continuous evacuation of the first collecting means.

9. An autologous blood collection system as defined in claim 8 wherein said second collecting means comprises a collapsible reservoir with resilience, the magnitude of the resilience being greater than the vacuum force within the first collecting means.

10. An autologous blood collection system as defined in claim 8 wherein said facilitating means comprises valve means situated between the first and second collecting means to assure unidirectional blood flow into and out of the second collecting means so that blood is collectible from the patient and infusible into the patient simultaneously.

11. An autologous blood collection system as defined in claim 8 wherein said closed extracorporeal blood circuit comprises a sterile, unbroken blood path from the point of collection to the point of infusion.

12. An autologous blood collection system comprising:
  means for aspirating blood from a patient;
  a first blood-receiving receptacle comprising means connected to the aspirating means for conducting blood from a patient to the interior of the first receptacle, means for imposing a continuous negative pressure within the first receptacle of sufficient magnitude to cause continuous aspiration of blood through the aspirating means, the first receptacle being sufficiently rigid that it will not significantly collapse upon imposition of the negative pressure;
  a second blood-receiving receptacle connected to the first by a hollow conduit which communicates the interior of the second receptacle with the interior of the first near the bottom of the first receptacle, said second receptacle comprising means for overcoming the continuous negative pressure in the first receptacle sufficiently enough to cause transfer of the blood to the second receptacle without interrupting the continuous aspiration of blood; and
  means for separating the second receptacle from the first without interrupting the continuous negative pressure in the first receptacle during the blood aspiration into the first receptacle.

13. An autologous blood collection system as defined in claim 12 further comprising an additional receptacle and means for connecting the additional receptacle to the first receptacle after separation of the second receptacle, the connecting means accommodating separation of the second receptacle and connection of the additional receptacle without interruption of the blood collection in the first receptacle.

14. An autologous blood collection system as defined in claim 12 wherein said second receptacle comprises means preserving the blood contents in a sterile environment for storage of same prior to infusion thereof into the patient.

15. A method of collecting blood from a patient and infusing the same blood back into the patient, comprising the steps of:
  providing a closed extracorporeal blood circuit through which blood passes;
  creating suction within a blood aspiration device and selectively aspirating blood from the patient through the blood aspiration device;
  depositing the blood in a first receptacle;
  transferring the blood from the first to a second receptacle;
  infusing the blood in the second receptacle into the patient without interrupting the suction within the blood aspiration device.

16. A method of collecting blood from a patient and infusing the same blood back into the patient as defined in claim 15 further comprising sterilizing the extracorporeal blood circuit and isolating the blood circuit from a suction source with a microorganism filter.

17. A method of collecting blood from a patient and infusing the same blood back into the patient as defined in claim 15 further comprising aspirating blood from the patient and simultaneously infusing the patient's own aspirated blood back into the patient.

18. A method of collecting blood from a patient and infusing the same blood back into the patient as defined in claim 15 further comprising the steps of developing a negative pressure in the first receptacle of sufficient magnitude to draw blood therein and imposing a force between the first and second receptacles which overcomes the negative pressure in the first receptacle thereby transferring blood into the second receptacle from the first, the blood transfer taking place without interrupting the negative pressure in the first receptacle.

19. A method of infusing autologous blood into a patient comprising the steps of:
  creating a negative pressure within a first receptacle and selectively delivering blood from the patient into the receptacle;
  overcoming the negative pressure in the first receptacle by exerting upon the blood a greater force toward a second receptacle to thereby transfer the blood into the second receptacle from the first without interrupting the negative pressure in the first receptacle; and
  infusing the blood in the second receptacle into the patient.

20. A method of infusing autologous blood into a patient as defined in claim 19 further comprising restricting the blood flow to unidirectional travel between the first and second receptacles.

21. A method of infusing autologous blood into a patient as defined in claim 19 wherein said infusing step is preceded by separating the second receptacle from the first without interrupting the negative pressure in the first receptacle.

22. A method of infusing autologous blood into a patient as defined in claim 21 further comprising connecting another receptacle to the first receptacle so as to transfer the blood collected in the first receptacle to the other receptacle, said connecting step being effected without interrupting the negative pressure in the first receptacle.

23. A method of infusing autologous blood into a patient as defined in claim 19 wherein said overcoming step includes venting the second receptacle into the first above the blood level to enable the blood to flow into the second receptacle.

24. A method of infusing autologous blood into a patient as defined in claim 19 wherein infusing step comprises conducting blood into the patient directly from the second receptacle without interrupting the delivery of blood from the patient into the first receptacle.

25. A method of infusing autologous blood into a patient as defined in claim 24 wherein said conducting step comprises physically collapsing the second receptacle to force the blood therein into the patient.

26. A method of collecting blood from a patient and infusing the same blood back into the patient, comprising the steps of:

providing a closed extracorporeal blood circuit through which blood passes;

creating suction within a blood-aspirating device and selectively aspirating blood from the patient through the blood-aspirating device;

depositing the blood in a first receptacle;

transferring the blood from the first to a second receptacle;

separating the second receptacle from the first without interrupting the suction within the blood-aspirating device; and infusing blood from the second receptacle into the patient.

27. A method of collecting blood from a patient and infusing the same blood back into the patient as defined in claim 26 further comprising sealing both the first and second receptacles upon separation.

28. A method of autologous blood transfusion comprising the steps of:

aspirating blood from a patient;

collecting the aspirated blood in a first receptacle;

filtering the blood collected in the first receptacle;

transferring the blood from a first to a second receptacle simultaneously with the collecting step; and separating the second receptacle from the first without interrupting the aspirating, collecting and filtering steps.

* * * * *

UNITED STATES PATENT AND TRADEMARK OFFICE
CERTIFICATE OF CORRECTION

PATENT NO. : 4,047,526

DATED : September 13, 1977

INVENTOR(S) : Gordon S. Reynolds, Karl A. Pannier, Jr. and James L. Sorenson

It is certified that error appears in the above-identified patent and that said Letters Patent are hereby corrected as shown below:

Column 4, line 36, "39" should be --30--
Column 5, line 56, "tabe" should be --tab--
Column 6, line 46, "firsr" should be --first--.

Signed and Sealed this

Tenth Day of January 1978

[SEAL]

Attest:

RUTH C. MASON
Attesting Officer

LUTRELLE F. PARKER
Acting Commissioner of Patents and Trademarks